US009006445B2

(12) United States Patent
Sonesson et al.

(10) Patent No.: US 9,006,445 B2
(45) Date of Patent: Apr. 14, 2015

(54) POLYMORPHIC FORM OF PRIDOPIDINE HYDROCHLORIDE (75) Inventors: Clas Sonesson, Billdal (SE); Thomas Pittelkow, Holmegaard (DK); Brian Frøstrup, Lyngby (DK); Anne Zimmermann, Copenhagen (DK)

(73) Assignee: Ivax International GmbH, Rapperswil (CH)

( * ) Notice: Subject to any disclaimer, the term of this patent is extended or adjusted under 35 U.S.C. 154(b) by 0 days.

(21) Appl. No.: 14/342,253

(22) PCT Filed: Sep. 6, 2012

(86) PCT No.: PCT/EP2012/067371
§ 371 (c)(1),
(2), (4) Date: Jul. 3, 2014

(87) PCT Pub. No.: WO2013/034622
PCT Pub. Date: Mar. 14, 2013

(65) Prior Publication Data
US 2014/0315951 A1    Oct. 23, 2014

Related U.S. Application Data (60) Provisional application No. 61/533,550, filed on Sep. 12, 2011.

(30) Foreign Application Priority Data
Sep. 7, 2011 (DE) ................... 2011 70496

(51) Int. Cl.
*C07D 211/20* (2006.01)
*C07D 211/30* (2006.01)
*C07D 211/24* (2006.01)

(52) U.S. Cl.
CPC ............ *C07D 211/30* (2013.01); *C07D 211/24* (2013.01)

(58) Field of Classification Search
USPC ......................................................... 546/236
See application file for complete search history.

(56) References Cited

U.S. PATENT DOCUMENTS

| | | | |
|---|---|---|---|
| 6,903,120 | B2 | 6/2005 | Sonesson et al. |
| 7,417,043 | B2 | 8/2008 | Sonesson et al. |
| 7,923,459 | B2 | 4/2011 | Gauthier et al. |
| 2007/0238879 | A1* | 10/2007 | Gauthier et al. ............ 546/236 |
| 2010/0105736 | A1 | 4/2010 | Wikström |
| 2013/0150406 | A1 | 6/2013 | Zimmermann et al. |
| 2013/0197031 | A1 | 8/2013 | Sonesson |
| 2013/0267552 | A1 | 10/2013 | Waters et al. |
| 2014/0088140 | A1 | 3/2014 | Hayden et al. |
| 2014/0088145 | A1 | 3/2014 | Hayden et al. |

FOREIGN PATENT DOCUMENTS

| | | |
|---|---|---|
| CN | 101056854 A | 10/2007 |
| WO | WO 01/46145 A1 | 6/2001 |
| WO | WO 2006/040155 | 4/2006 |
| WO | WO 2006/040155 A1 | 4/2006 |

OTHER PUBLICATIONS

Zimmermann et al. "Polymorphs of Pridopidine Hydrochloride", Crystal Growth & Design, vol. 12, No. 6, Jun. 6, 2012.*
Zimmermann et al. (2012). Polymorphs of Pridopidine Hydrochloride. *Crystal Growth & Design*, 12(6), 2961-2968.
Notification of Transmittal of the International Search Report and the Written Opinion of the International Searching Authority, or the Declaration, including an International Search Report and Written Opinion of the International Searching Authority, mailed Oct. 18, 2012 in connection with PCT International Application No. PCT/EP2012/067371, filed Sep. 6, 2012.
Notification Concerning Transmittal of International Preliminary Report on Patentability (Chapter I of the Patent Cooperation Treaty), including an International Preliminary Report on Patentability and Written Opinion of the International Searching Authority, mailed Mar. 20, 2014 by the International Bureau of WIPO in connection with PCT International Application No. PCT/EP2012/067371, filed Sep. 6, 2012.
U.S. Appl. No. 14/309,111, Merav Bassan et al.
May 17, 2013 Office Action in connection with U.S. Appl. No. 13/708,816.
Aug. 16, 2013 Amendment in response to May 17, 2013 Office Action in connection with U.S. Appl. No. 13/708,816.
Nov. 5, 2013 Final Office Action issued in connection with U.S. Appl. No. 13/708,816.
Feb. 5, 2014 Response to Nov. 5, 2013 Final Office Action issued in connection with U.S. Appl. No. 13/708,816.
Mar. 11, 2014 Advisory Action issued in connection with U.S. Appl. No. 13/708,816.
May 5, 2014 Response to Nov. 5, 2013 Final Office Action and Mar. 11, 2014 Advisory Action in connection with U.S. Appl. No. 13/708,816.
Jun. 18, 2014 Office Action in connection with U.S. Appl. No. 13/708,816.
Oct. 28, 2014 Notice of Allowance issued in connection with U.S. Appl. No. 13/708,816.
International Preliminary Report on Patentability issued Jun. 10, 2014 including Notification of Transmittal of the International Search Report and the Written Opinion of the International Searching Authority, or the Declaration, including an International Search Report and Written Opinion of the International Searching Authority, mailed Feb. 22, 2013 in connection with PCT International Application No. PCT/US2012/68582 filed Dec. 7, 2012.

(Continued)

*Primary Examiner* — Nizal Chandrakumar
(74) *Attorney, Agent, or Firm* — John P. White; Gary J. Gershik; Cooper & Dunham LLP (57) ABSTRACT

This invention relates to a new crystalline form of Pridopidine, a drug substance currently in development for the treatment of Huntington's disease. More specifically the invention provides polymorphic Form II of the Pridopidine hydrochloride salt, a process for the preparation of this polymorphic form, pharmaceutical compositions comprising polymorphic Form II, and methods of uses of this polymorphic form.

5 Claims, 11 Drawing Sheets

(56) References Cited

OTHER PUBLICATIONS

Feb. 3, 2014 Opposition filed against Venezuelan Patent Application No. 001610-2012 by CIFAR.

Apr. 22, 2014 response to Feb. 3, 2014 Opposition filed against Venezuelan Patent Application No. 001610-2012 by CIFAR.

Nov. 19, 2014 Office Action issued by the Chinese Patent Office in connection with Chinese Patent Application No. 201280043794.9 (including English Language Translation of the cover pages).

Ludin et al., "Efficacy and Safety of the Dopaminergic Stabilizer Pridopidine (ACR16) in Patients With Huntington's Disease" Clinical Neuropharmacology, Sep./Oct. 2010—vol. 33—Issue 5—pp. 260-264, abstract.

* cited by examiner

POLYMORPHIC FORM OF PRIDOPIDINE HYDROCHLORIDE

CROSS-REFERENCE TO RELATED APPLICATIONS

This application is a §371 national stage of PCT International Application No. PCT/EP2012/067371, filed Sep. 6, 2012, claiming the benefit of U.S. Provisional Application No. 61/533,550, filed Sep. 12, 2011 and priority of Danish Patent Application No. PA 2011 70496, filed Sep. 7, 2011, the contents of each of which are hereby incorporated by reference in their entirety.

TECHNICAL FIELD

This invention relates to a new crystalline form of Pridopidine, a drug substance currently in development for the treatment of Huntington's disease. More specifically the invention provides polymorphic Form II of the Pridopidine hydrochloride salt, a process for the preparation this polymorphic form, pharmaceutical compositions comprising polymorphic Form II, and methods of uses of this polymorphic form.

BACKGROUND ART

Polymorphism in material science is the ability of a solid material to exist in more than one crystal form with each form having different orientations and/or conformations of the molecules in the crystal lattice. Polymorphism is important in the development of pharmaceutical ingredients, because each polymorph exhibits a unique set of physicochemical properties, due to the differences in structural arrangements in the crystals. Thus, solubility and dissolution rate may vary between polymorphs, leading to potential differences in bioavailability. Furthermore, mechanical properties such as flowability and compactability, which affect the processing properties of a compound, may be different. Stability and shelf life of a compound may also depend on the chosen polymorph. For these reasons it is valuable to screen for the existence of different polymorphic forms and to characterize discovered forms. Having different polymorphic forms to choose from provides new opportunities to improve the performance of a pharmaceutical product.

The polymorphic outcome of a chemical synthesis is determined by the crystallization conditions such as choice of solvent(s), rate of solvent addition, temperature, stirring rate, level of super-saturation, and level of impurities. Hence, different crystallization processes may give rise to different polymorphs. Polymorphs also have different stabilities and may spontaneously convert from one form to another.

Polymorphs can be distinguished from each other by a variety of techniques. Polymorphs exhibit distinct spectroscopic properties and can be identified using infrared spectroscopy, raman spectroscopy, and $^{13}$C-NMR spectroscopy. Due to the fact that each crystal form diffracts X-rays in different ways, X-ray powder diffractometry (XRPD) can also be used for identification. Furthermore, thermal methods such as differential scanning calorimetry (DSC) and thermogravimetric analysis (TGA) can provide information unique to a particular polymorph.

Pridopidine, i.e. 4-(3-methanesulfonyl-phenyl)-1-propyl-piperidine, is a drug substance currently in clinical development for the treatment of Huntington's disease. The hydrochloride salt of 4-(3-methanesulfonyl-phenyl)-1-propyl-piperidine and a method for its synthesis is described in WO 01/46145. In WO 2006/040155 an alternative method for the synthesis of 4-(3-methanesulfonyl-phenyl)-1-propyl-piperidine is described. When following these routes of synthesis a crystalline phase results with a melting point of 199° C. This crystalline phase is designated Form I.

Figure 1:
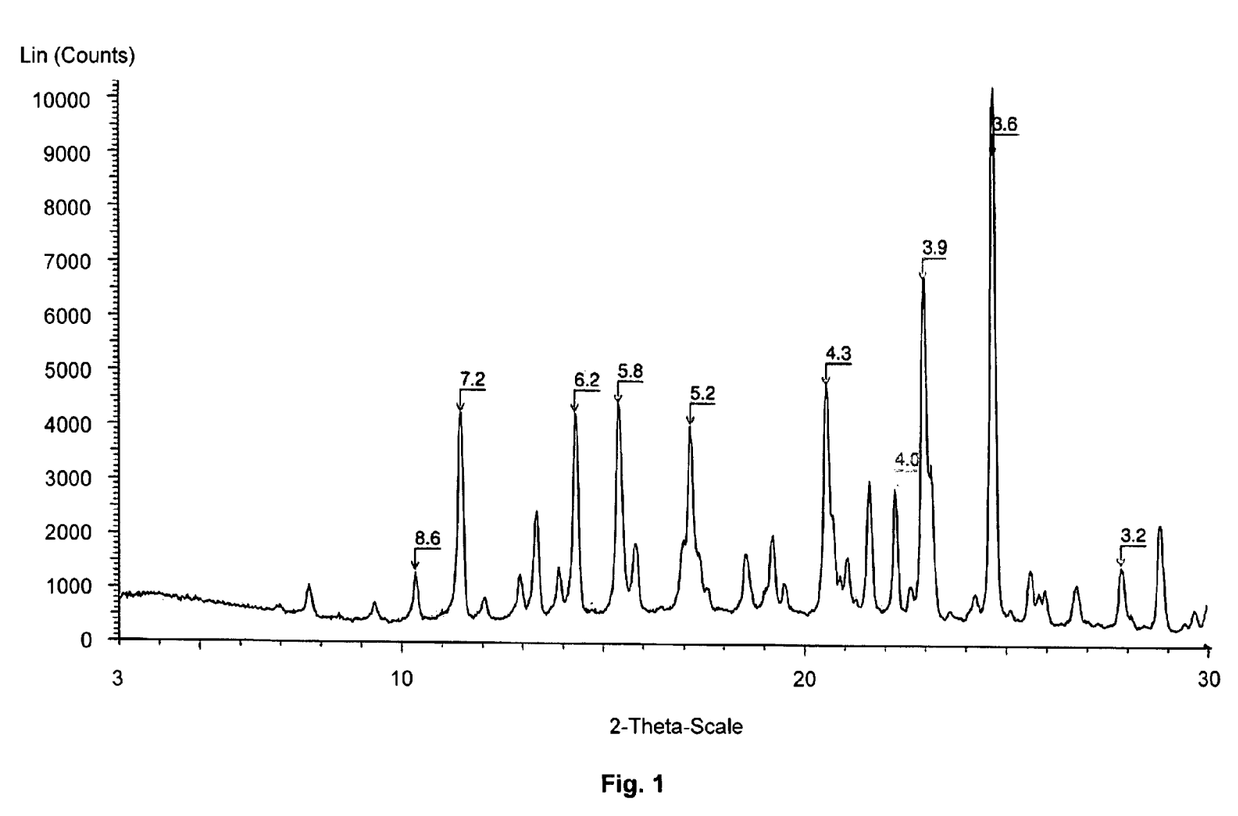
FIG. 1 shows a characteristic X-ray powder diffraction pattern of crystalline Pridopidine hydrochloride Form I.
Figure 2:
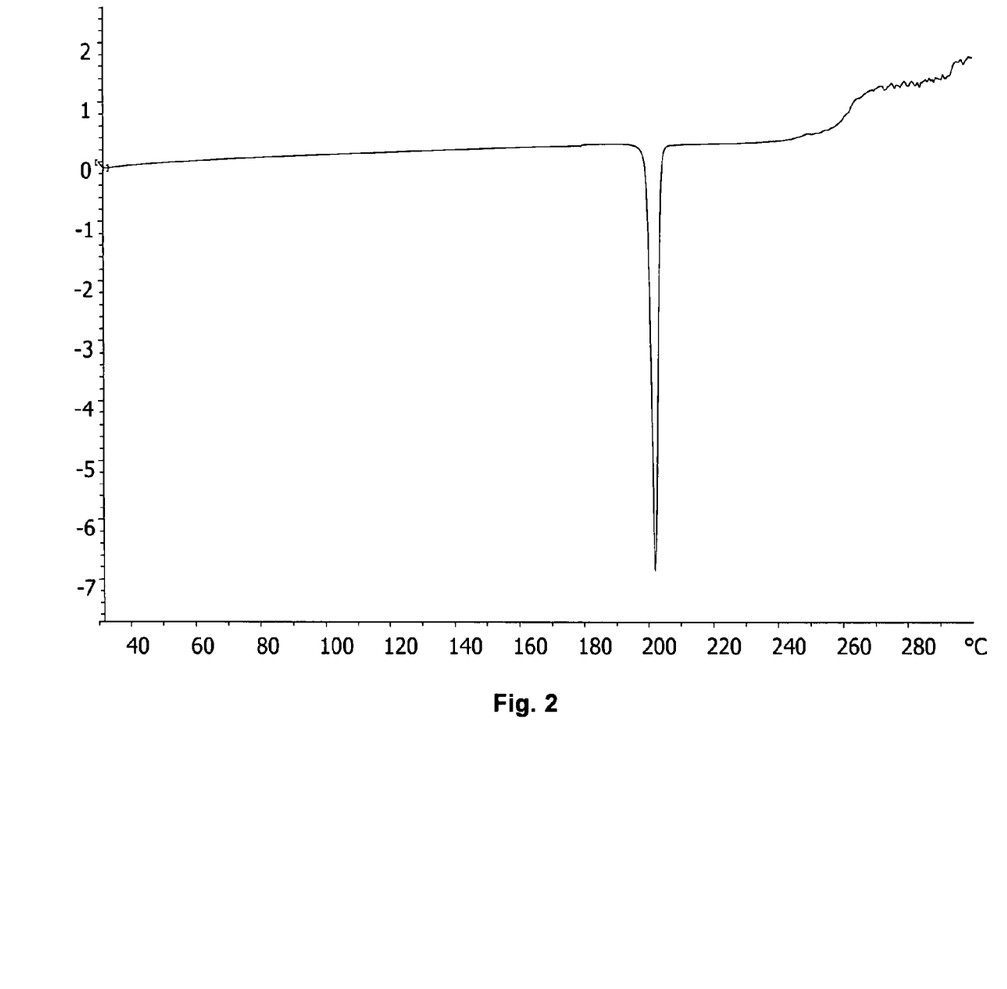
FIG. 2 shows a characteristic DSC thermogram of crystalline Pridopidine hydrochloride Form I.
Figure 3:
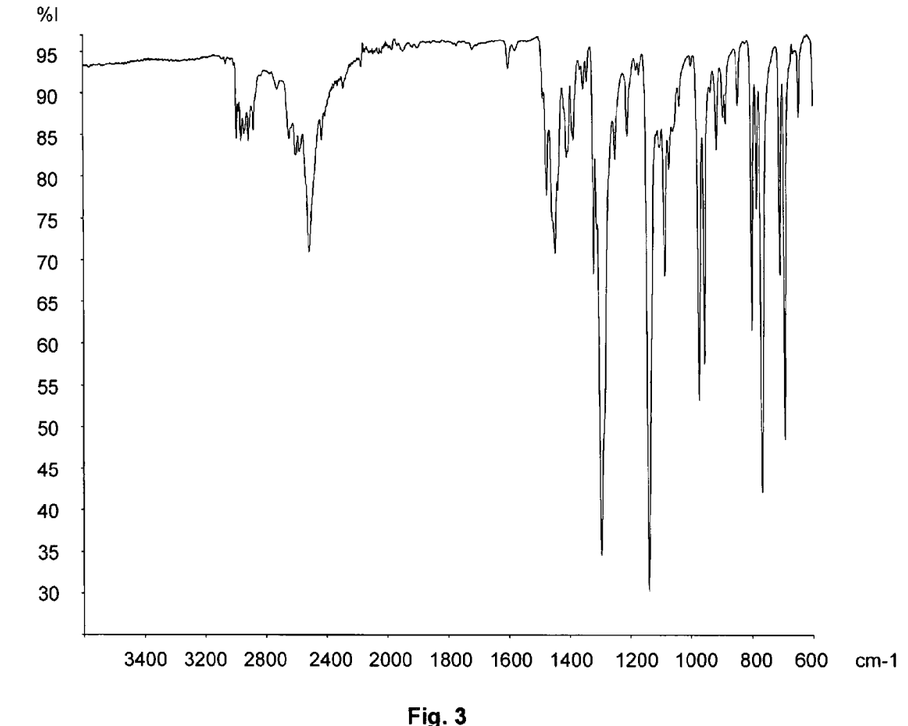
FIG. 3 shows a characteristic FT-IR spectrum of crystalline Pridopidine hydrochloride Form I.
Figure 4:
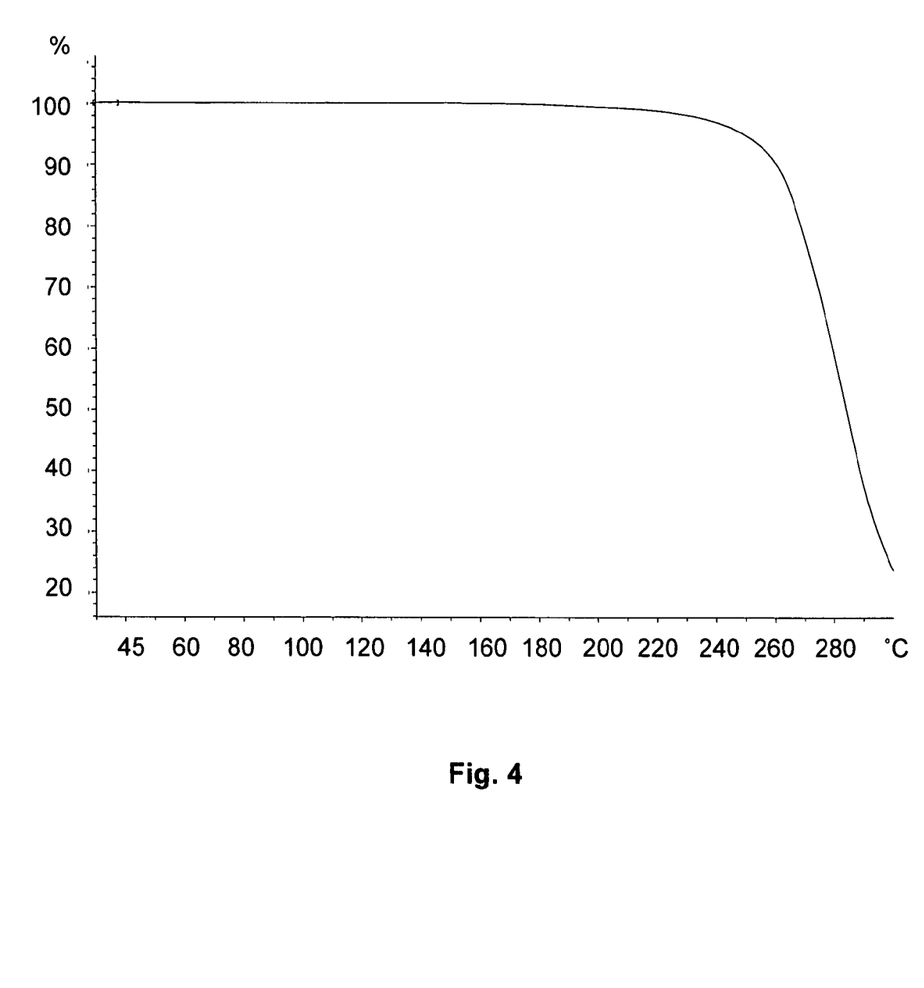
FIG. 4 shows a characteristic TGA thermogram of crystalline Pridopidine hydrochloride Form I.

Pridopidine hydrochloride Form I crystallises in the orthorhombic space group Pna2$_1$, with the lattice parameters a=10.5 Å, b=23.1 Å, c=6.9 Å, α=90° C., β=90° C., γ=90° C., and cell volume 1682 Å$^3$. Form I is characterised by an X-ray powder diffractogram having the characteristic d-spacing's shown in Table 1, below, or a diffractogram substantially as depicted in FIG. 1; a DSC thermogram substantially as shown in FIG. 2, having an endotherm with an onset of about 199° C.; an IR spectrum substantially as depicted in FIG. 3; and a TGA thermogram substantially as depicted in FIG. 4.

TABLE 1

| d-spacing's, Pridopidine hydrochloride, crystalline Form I | | | | | | | | | |
|---|---|---|---|---|---|---|---|---|---|
| 8.6 | 7.2 | 6.2 | 5.8 | 5.2 | 4.3 | 4.0 | 3.9 | 3.6 | 3.2 |

Figure 5:
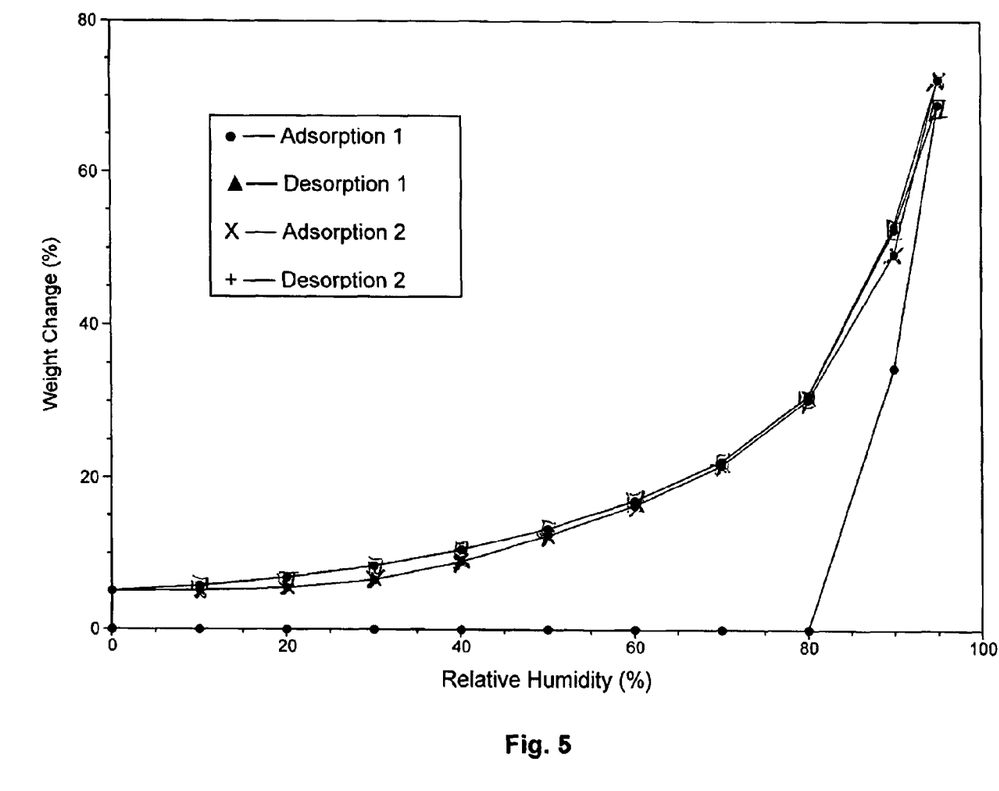
FIG. 5 shows a characteristic dynamic vapour sorption (DVS) profile of crystalline Pridopidine hydrochloride Form I in the relative humidity range 0-95%.

The dynamic vapour sorption (DVS) profile shows that Form I is non-hygroscopic below 80% RH, but deliquescent in excess of 80% RH (FIG. 5). TGA shows Form I to be a non-solvated form (FIG. 4). Form I is highly soluble in aqueous liquids with solubility in water of above 200 mg/ml.

The particle size—and shape distributions for Form I was investigated using image analysis and presented in Table 2 below. The $D_{50}$ is 21 µm, and the $D_{10}$ and $D_{90}$ are 9 and 42 µm, respectively. The aspect ratio (AR) is obtained by dividing the longest dimension of the particles with the shortest one. Since the $AR_{50}$ is 3.1 the particles are needle shaped.

TABLE 2

| Particle size (µm) | $D_{10}$ | 9 |
|---|---|---|
|  | $D_{50}$ | 21 |
|  | $D_{90}$ | 42 |
| Aspect ratio | $AR_{10}$ | 1.6 |
|  | $AR_{50}$ | 3.1 |
|  | $AR_{90}$ | 5.8 |

The bulk density and tapped density of Form I are 0.212 g/ml ±2.2%, and 0.264 g/ml ±1.1%, respectively.

A polymorph screening was performed on Pridopidine hydrochloride, including various methods of crystallization such as slurrying in organic solvents, solvent evaporation, cooling crystallization, crash cooling, and anti solvent addition. A wide selection of solvents was employed in order to increase the chance of finding new polymorphic forms. However, no forms besides the known Form I were discovered in the screening.

SUMMARY OF THE INVENTION

The discovery of new polymorphic forms of a drug substance provides new opportunities to improve the performance characteristics of the drug. Crucial parameters such as melting point, hygroscopicity and crystallinity are of paramount importance in the selection of the most suitable form of the drug. In addition, bulk properties such as particle size and shape can affect the manufacturing of a drug product.

Prodopidine is being developed as a hydrochloride salt, and the present invention is directed to the crystalline Form II of the hydrochloride salt. This crystalline form was not discovered during the development of the synthesises described in WO 01/46145 and WO 2006/040155, above, and it was not found in a polymorph screening which, as described above, was designed to facilitate crystallization of new solid forms. Thus, the existence of Form II was not obvious.

According to the present invention a new polymorph of the 4-(3-methanesulfonyl-phenyl)-1-propyl-piperidine hydrochloride salt is identified, and a process for its preparation is provided.

In another aspect pharmaceutical compositions comprising a therapeutically effective amount of the 4-(3-methanesulfonyl-phenyl)-1-propyl-piperidine hydrochloride salt according to the invention, together with one or more adjuvants, excipients, carriers and/or diluents.

Viewed from another aspect the invention relates to the 4-(3-methanesulfonyl-phenyl)-1-propyl-piperidine hydrochloride of the invention for use as a medicament.

In a further aspect the invention provides a method of treatment, prevention or alleviation of a dopamine mediated disorder, which method comprises the step of administering to such a living animal body in need thereof, a therapeutically effective amount of the 4-(3-methanesulfonyl-phenyl)-1-propyl-piperidine hydrochloride salt of the invention.

Other objects of the invention will be apparent to the person skilled in the art from the following detailed description and examples.

DETAILED DISCLOSURE OF THE INVENTION

Pridopidine is a dopaminergic stabilizer currently in development for the treatment of Huntington's disease. The drug substance is a weak base in the form of a tertiary amine with a calculated pKa value of 8.9.

4-(3-methanesulfonyl-phenyl)-1-propyl-piperidine; Pridopidine

Figure 6:
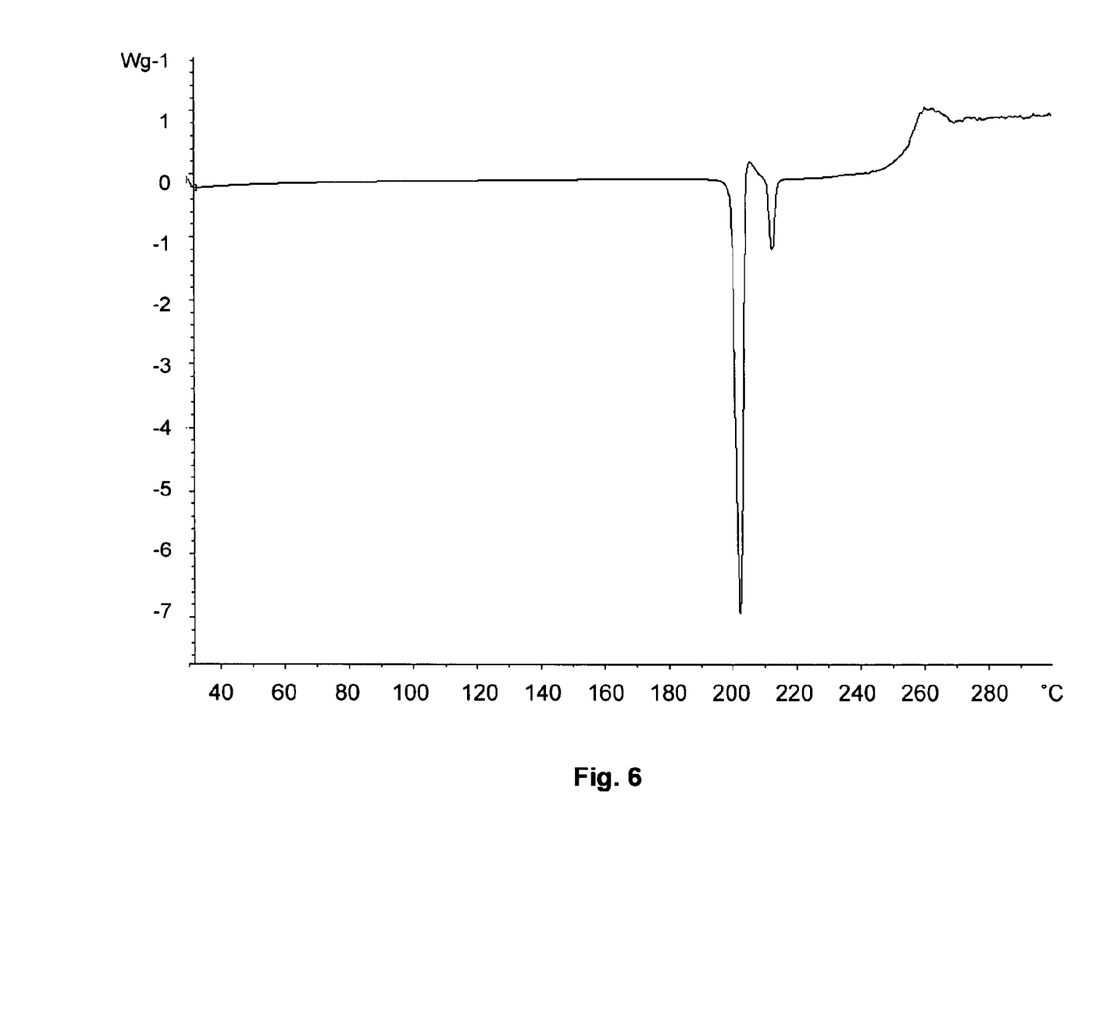
FIG. 6 shows a DSC thermogram of crystalline Pridopidine hydrochloride Form I, where endotherms characteristic of both Form I (199° C.) and Form II (210° C.) are present.

A new crystalline form of Pridopidine hydrochloride, Form II, was discovered during DSC analysis of Form I. For some Form I batches, the DSC thermogram showed an extra endotherm with an onset of about 210° C., following the Form I melting endotherm at around 199° C. (FIG. 6). This indicated the existence of a new crystalline phase. In order to isolate this crystal phase, a sample of Form I was heated to 203° C., followed by cooling. XRPD of the resulting solid phase showed that a new solid form had been formed, and this form has been designated Form II.

Accordingly, in its first aspect the invention provides a new crystalline form, Form II, of 4-(3-methanesulfonyl-phenyl)-1-propyl-piperidine hydrochloride salt, or a solvate thereof.

In a preferred embodiment the crystalline Form II is provided in an anhydrous form.

In another preferred embodiment the crystalline Form II is provided in an anhydrous form and non-solvated form.

Figure 7:
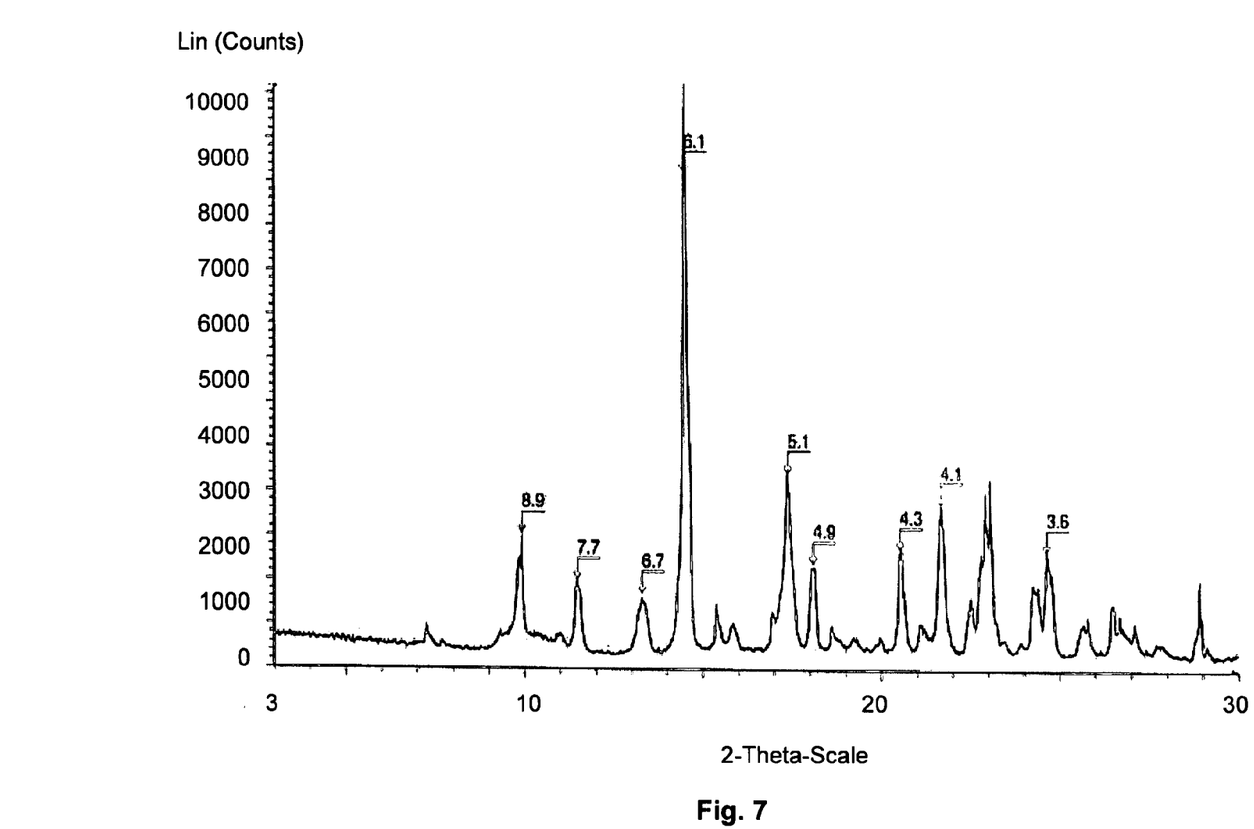
FIG. 7 shows a characteristic X-ray powder diffraction pattern of crystalline Pridopidine hydrochloride Form II.

The crystalline Form II of the invention is characterised by a powder X-ray diffractogram having the d-spacing's shown in Table 3, below, or a diffractogram substantially as depicted in FIG. 7.

TABLE 3

| d-spacing's, Pridopidine hydrochloride, crystalline Form II | | | | | | | | |
|---|---|---|---|---|---|---|---|---|
| 8.9 | 7.7 | 6.7 | 6.1 | 5.1 | 4.9 | 4.3 | 4.1 | 3.6 |

Therefore, in a third preferred embodiment, the crystalline 4-(3-methanesulfonyl-phenyl)-1-propyl-piperidine hydrochloride salt of the invention is characterized by having an X-ray powder diffraction pattern with reflections corresponding to the d-spacing values 6.1 and 4.9.

In a more preferred embodiment, the crystalline Form II of the invention is characterized by having an X-ray powder diffraction pattern with reflections corresponding to the d-spacing values 8.9 and 4.1.

In a third more preferred embodiment, the crystalline Form II of the invention may be characterized by having an X-ray powder diffraction pattern with reflections corresponding to the d-spacing values 8.9, 7.7, 6.7, 6.1, 5.1, 4.9, 4.3, 4.1 and 3.6.

Figure 8:
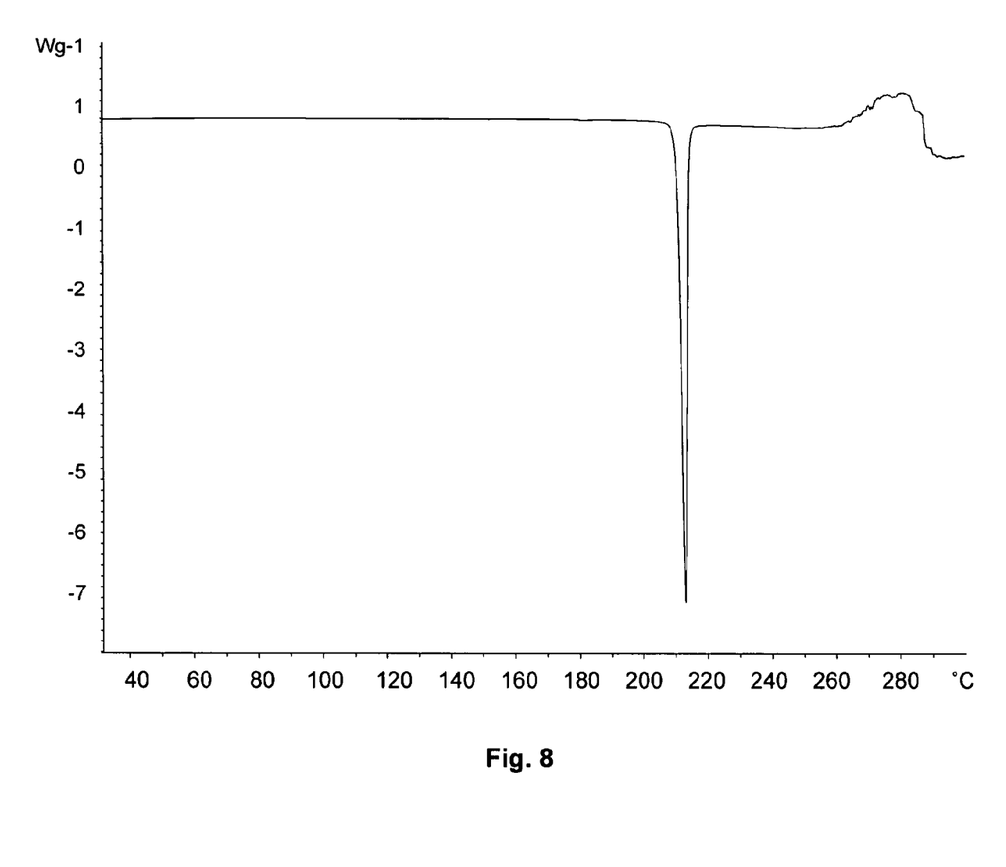
FIG. 8 shows a characteristic DSC thermogram of crystalline Pridopidine hydrochloride Form II.

In a third preferred embodiment, the crystalline Form II of the invention may be characterized by having a DSC thermogram substantially as shown in FIG. 8.

In a fourth preferred embodiment, the crystalline Form II of the invention may be characterized by having an endotherm with an onset of about 210° C., as obtained with DSC.

Figure 9:
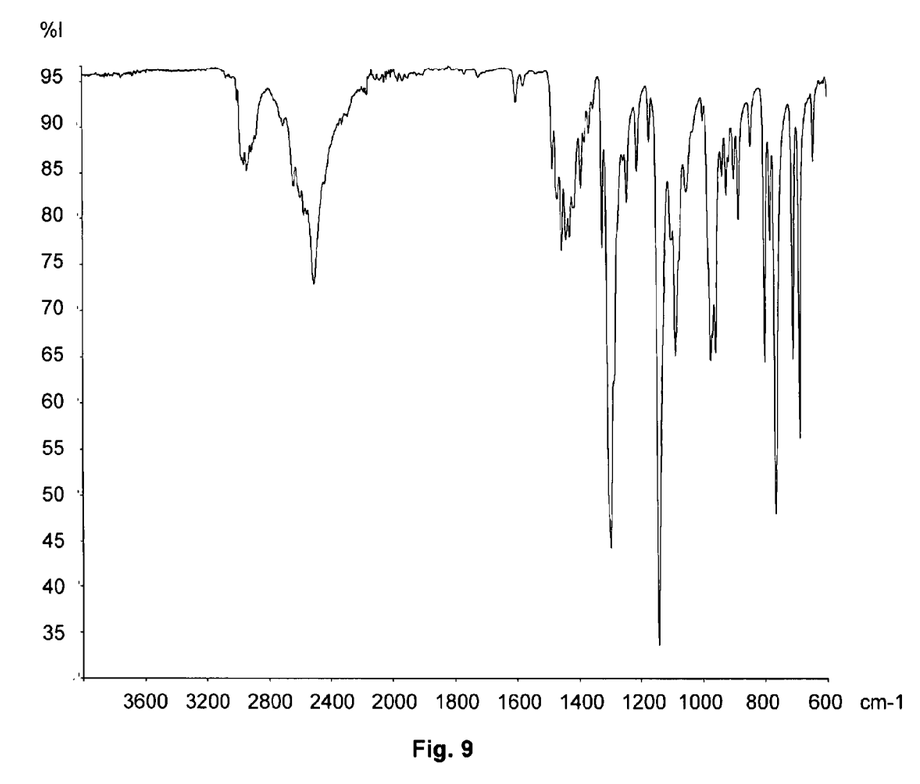
FIG. 9 shows a characteristic FT-IR spectrum of crystalline Pridopidine hydrochloride Form II.

In a fifth preferred embodiment, the crystalline Form II of the invention may be characterized by having an IR spectrum substantially as depicted in FIG. 9.

Figure 10:
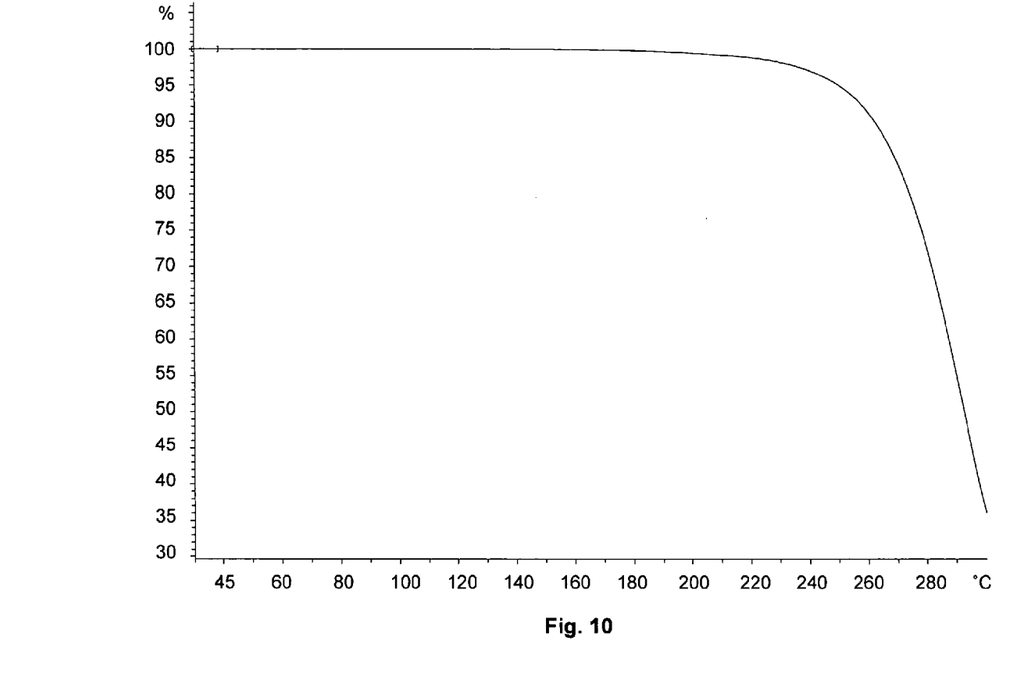
FIG. 10 shows a characteristic TGA thermogram of crystalline Pridopidine hydrochloride Form II.

In a sixth preferred embodiment, the crystalline Form II of the invention may be characterized by having a TGA thermogram substantially as depicted in FIG. 10.

Figure 11:
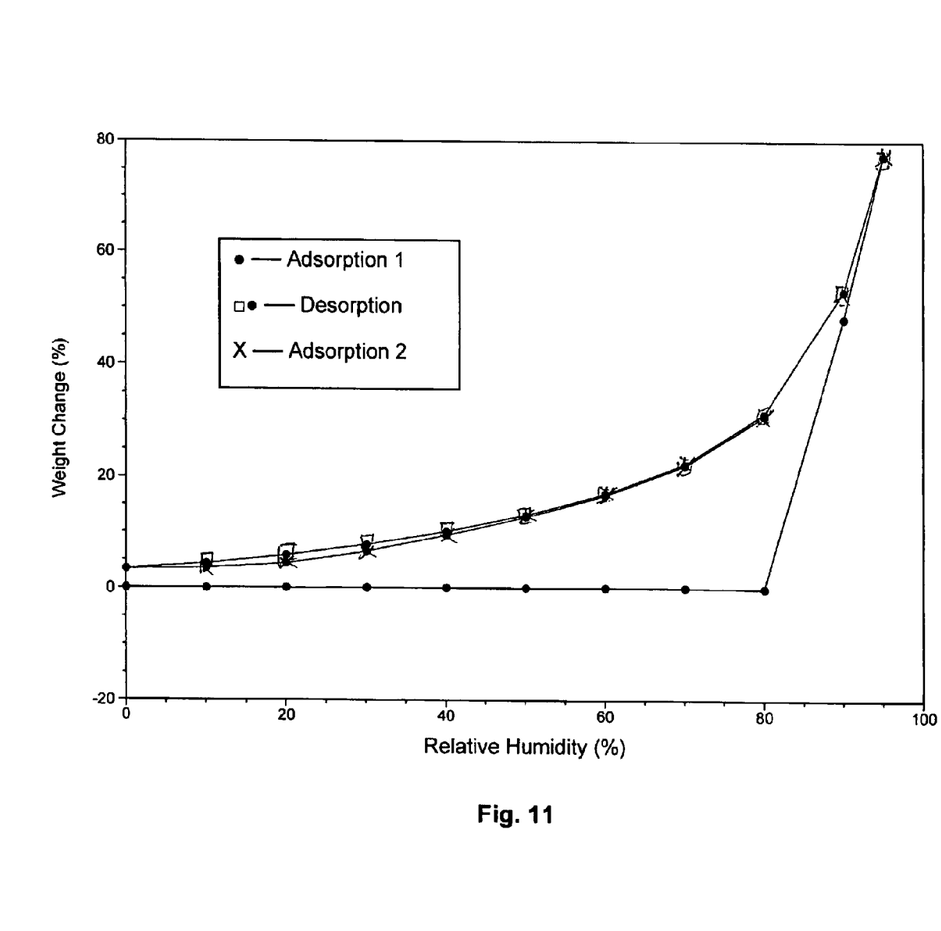
FIG. 11 shows a characteristic dynamic vapour sorption (DVS) profile of crystalline Pridopidine hydrochloride Form II in the relative humidity range 0-95%.

Form II crystallises in the monoclinic space group $P2_1/c$, with the lattice parameters a=12.2 Å, b=13.5 Å, c=10.2 Å, $\alpha$=90° C., $\beta$=91.1° C., $\gamma$=90° C., and cell volume 1685 Å$^3$. The dynamic vapour sorption (DVS) profile shows that Form II is non-hygroscopic below 80% RH, but deliquescent in excess of 80% RH (FIG. 11). TGA shows Form II to be a non-solvated form (FIG. 10), and Karl Fisher analysis confirmed the anhydrous nature of the salt. The solubility of Form II at room temperature could not be determined, as Form II transforms rapidly to Form I when exposed to solvent.

Only one polymorphic form is thermodynamically stable at a given temperature. Therefore it is of interest to determine which polymorph is the most stable one at ambient temperature, and how the stability relationship between the polymorph is affected by a change in temperature. The stability at ambient temperature was determined by exposing both forms to solvent to form a slurry. When exposed to solvent, Form II rapidly transformed into Form I, and from this it is concluded that Form I is the stable form at ambient temp.

The relative thermodynamic stability of the forms as a function of temperature was investigated based on thermal data. According to the heat of fusion rule proposed by Burger & Ramberger (Burger A and Ramberger R: On the polymorphism of pharmaceuticals and other molecular crystals; *I. Mikrochim. Acta.* II 1979 259-271), the polymorphs are enantiotropically related, as Form II has a higher melting point and a lower heat of fusion than Form I. Form I has a melting point of 199° C. and a heat of fusion of 34.8 KJ/mol, while Form II has a melting point of 210° C. and a heat of fusion of 32.0 KJ/mol, as determined by DSC.

In a seventh preferred embodiment, the crystalline 4-(3-methanesulfonyl-phenyl)-1-propyl-piperidine hydrochloride salt of the invention is characterized by having a DSC thermogram substantially as shown in FIG. 8, and by having an endotherm with an onset of about 210° C.

When two forms are enantiotropically related it is of interest to determine the transition temperature ($T_t$) in order to be able to control the outcome of synthesis and pharmaceutical processing. Lian Yu (Yu L: Inferring thermodynamic stability relationship of polymorphs from melting data; *J. Pharm. Sci.* 1995 84 966-974) has proposed a model where $T_t$ can be calculated based on melting points and heats of fusion. Applying this method, a $T_t$ of 127° C. was obtained. In order to confirm this finding experimentally, a seeding experiment was carried out, where mixtures of the two forms were slurried in an organic solvent for 4 hours at various temperatures.

Following slurrying, the identity of the resulting solid phase was determined by XRPD. At temperatures below 125° C., the polymorphic outcome was Form I, and above 130° C. the outcome was Form II. Hence, the study indicates that Form I and II are enantiotropically related, with Form I being the most stable form at room temperature, and Form I being the most stable form at temperatures above 127° C.

The particle size—and shape distributions for Form II was investigated using image analysis and presented in Table 4 below. The $D_{50}$ is 170 μm, and the $D_{10}$ and $D_{90}$ are 49 and 363 μm, respectively. The aspect ratio (AR) is obtained by dividing the longest dimension of the particles with the shortest dimension. Since the $AR_{50}$ for Form II is 1.6 compared to 3.1 for Form I, the Form II crystals are less needle shaped than the Form I crystals. This may be an advantage in terms of pharmaceutical processing, where needle shaped particles are known to affect the flow and compression properties of the powder.

TABLE 4

| Particle size (μm) | $D_{10}$ | 49 |
|---|---|---|
| | $D_{50}$ | 170 |
| | $D_{90}$ | 363 |
| Aspect ratio | $AR_{10}$ | 1.1 |
| | $AR_{50}$ | 1.6 |
| | $AR_{90}$ | 2.9 |

The bulk density and tapped density of Form II are 0.382 g/ml ±0.3%, and 0.486 g/ml ±1.1%, respectively, which is much higher than the densities of Form I (see Table 2). This may have implication for instance during formulation of capsules, where smaller hard gelatin capsules could be used to administrate the same amount of Form II compared to Form I.

Methods of Preparation

Form II of pripopidine hydrochloride is thermodynamically stable above 127° C., and hence it should be possible to prepare Form II be re-crystallization of Form I at elevated temperature. However, attempt to prepare Form II by re-crystallization of Form I at temperatures above 127° C. without addition of seed crystals of Form II were unsuccessful.

In order to successfully prepare Form II is was necessary to produce Form II seed crystals by heating solid Form I to 203° C. to allow melting of Form I and re-crystallization to Form II, followed by cooling. This was done in a TGA oven. Seed crystals prepared in this way were used to prepare Form II. Form I was dissolved in 1,2-di-chlorobenzene at 165° C. to form a clear solution. The Form II seed crystals were added and the seeded solution was left to crystallise at 165° C. The formed suspension was filtered at 150° C. and the crystals were dried under vacuum.

Biological Activity

WO 01/46145, WO 01/46146, WO 2005/121087, WO 2007/042295 WO 2008/127188 and WO 2008/155357 all describe substituted 4-phenyl-N-alkyl-piperazines and 4-phenyl-N-alkyl-piperidines, reported to be modulators of dopamine neurotransmission, and to be useful in treatment of symptoms of various disorders of the central nervous system. The 4-(3-methanesulfonyl-phenyl)-1-propyl-piperidine hydrochloride salt of the invention is considered useful for the same medical indications as described in these publications, and these publications therefore are incorporated by reference.

Neurological indications contemplated according to these publications include the treatment of Huntington's disease and other movement disorders, as well as movement disorders induced by drugs.

Therefore, in a preferred embodiment, the invention relates to the use of the 4-(3-methanesulfonyl-phenyl)-1-propyl-piperidine hydrochloride salt of the invention for use as a medicament for the treatment of Huntington's disease.

Pharmaceutical Compositions

Viewed from another aspect the invention provides 4-(3-methanesulfonyl-phenyl)-1-propyl-piperidine hydrochloride salt, or a solvate thereof, in a crystalline form (Form II), for use as medicaments. Therefore, in another aspect, the invention provides novel pharmaceutical compositions comprising a therapeutically effective amount of the compound of the invention.

While a compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

Pharmaceutical compositions of the invention may in particular be formulated as described in WO 01/46145.

Further details on techniques for formulation and administration may be found in the latest edition of *Remington's Pharmaceutical Sciences* (Maack Publishing Co., Easton, Pa.).

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 1 to about 500 mg of active ingredient per individual dose, preferably of from about 10 to about 100 mg, most preferred of from about 25 to about 50 mg, are suitable for therapeutic treatments. The daily dose will preferably be administered in individual dosages 1 to 4 times daily.

Methods of Therapy

In another aspect the invention provides a method for the treatment, prevention or alleviation of a dopamine mediated disorder of a living animal body, including a human, which method comprises the step of administering to such a living animal body in need thereof a therapeutically effective amount of the 4-(3-methanesulfonyl-phenyl)-1-propyl-piperidine hydrochloride salt of the invention.

In a preferred embodiment the dopamine mediated disorder is Huntington's disease.

BRIEF DESCRIPTION OF THE DRAWINGS

The present invention is further illustrated by reference to the accompanying drawing, in which.

EXAMPLES

The invention is further illustrated with reference to the following examples, which are not intended to be in any way limiting to the scope of the invention as claimed.

Example 1

Preparation of Pridopidine Form II

In order to prepare Form II on a larger (gram) scale is was necessary to first produce Form II seed crystals in mg scale. This was done by heating solid Form I to 203° C. to allow melting of Form I and subsequent re-crystallization to Form II, followed by cooling. This took place in a TGA oven. In this way approximately 10 mg of Form II was prepared.

To prepare Form II, 15 g of Pridopidine Form I was dissolved in 375 ml 1,2-di-chlorobenzene under heating to reflux at approximately 180° C. A clear solution was formed at around 165° C. The solution was transferred to an oil bath of 165° C. and seed crystals of Pridopidine Form II were added. Stirring was started as soon as the seed crystals started to grow. Over 30 minutes the temperature was lowered to 150° C. After another 30 minutes, the suspension was filtered at 150° C., followed by washing with heptane. The crystals were dried under vacuum: m.p. 210° C. The results of a CHN analysis are presented in Table 5, below.

NMR $^1$H NMR (DMSO-$d_6$): 0.93 (3H, t), 1.73-1.79 (2H, m), 2.00-2.13 (4H, m), 2.96-3.06 (5H, m), 3.23 (3H, s),3.54-3.57 (2H, m), 7.61-7.67 (2H, m), 7.79-7.84 (2H, m), 10.52 (1H, bs)

TABLE 5

| Elemental analysis | Result W/W % (n = 2) | | |
|---|---|---|---|
| Element | C | H | N |
| Theoretical content Anhydrous Pridopidine | 56.68 | 7.61 | 4.41 |
| Measured | 56.30 | 7.61 | 4.30 |

Example 2

Polymorph Screening of Pridopidine

A polymorph screening was performed on Pridopidine to see if solid forms alternative to Form I could be formed by various methods of crystallization using various solvents. The following solvents and solvent mixtures were applied.

> Ethanol
> Ethanol:water 90:10
> Acetone
> Acetone:water 90:10
> Dimethyl sulfoxide (DMSO)
> NN-dimethylacetamide (DMA)
> N-methylpyrrolidone (NMP)
> 1-butanol
> 2-propanol
> Toluene
> Tetrahydrofuran (THF)
> Acetonitrile
> Acetonitrile:water 90:10
> Ethyl acetate In the following a description of each experiment is given.

Slurrying in Solvents

A starting amount of the Pridopidine was added to small, clear Eppendorf plastic vials. The appropriate solvent/solvent mixture was added and the vial put on a rotamixer overnight. If a clear solution could be observed in that time, more compound was added and the vial put back on the rotamixer. This was continued until a solution containing solid Pridopidine could be observed in all vials. Total equilibration time was 7 days. The dried precipitate was examined by XRPD.

Solvent Evaporation

The supernatants generated during the slurry experiments were covered with pierced parafilm and left at room temperature in the dark. High boiling solvents were evaporated in a vacuum oven at 40° C. Dried precipitates were analyzed by XRPD.

Cooling Crystallization

Saturated solutions of Pridopidine were prepared in good solvents at 50° C. using a water bath. The solutions were covered and left in the refrigerator for a week. Dried precipitates were analyzed by XRPD.

Crash Cooling

Saturated solutions of Pridopidine were prepared in good solvent at 50° C. using a water bath. The solutions were crash cooled by placing them in a dry ice-salt mixture for a few minutes. If precipitation did not occur instantly, the solutions were kept in the freezer until the next day. The supernatant was removed and the dried material was analyzed by XRPD.

Non-solvent Precipitation

Saturated solutions of Pridopidine were prepared in good solvents at 50° C. using a water bath. To these solutions, cold (room temp.) non-solvents were added drop wise until the solution volume had been doubled. The supernatant was removed and the dried material was analyzed by XRPD.

Compression

Pridopidine powder was filled into the die of a hydraulic IR-press. The die was placed in the press and the powder was compressed for 24 hours at 10 T. The compressed material was analyzed by XRPD.

XRPD analyses showed that all of the formed material was Form I.

Example 3

Analytical Methods

X-ray Powder Diffraction

X-ray powder diffraction (XRPD) experiments were conducted using a Bruker D8 Advance diffractometer configured as listed below:

| | |
|---|---|
| Goniometer | Theta-theta |
| Geometry | Bragg-Brentano geometry. |
| Primary slit | 1.0 mm and 2.5° soller slit |
| Secondary collimator | 1.0 mm and 2.5° Soller slit |
| Detector slit | 0.1 mm |
| Monochromator | Ni-filter |
| Detector | Scintillation counter |
| Scan range | 3-30°, 2 Theta |
| Scan speed | 5 s/step, 0.020° 2 theta/step |
| Radiation | CuK |
| Generator | 40 kV, 40 mA |
| Sample stage | 9 position, spinning mode |

The sample was placed on a zero back ground silicon single crystal sample holder in a thin film of vaseline. The diffractograms were acquired using Bruker "XRD Commander", ver. 2.6.1, and was evaluated using "Bruker Evaluation", ver. 11,0,0,3.

Following his procedure the d-spacing's shown in Table 3, and the diffractogram shown in FIG. 7 were obtained.

Differential Scanning Calorimetry

Differential scanning calorimetry (DSC) experiments were conducted on a Mettler Toledo DSC 821e Differential Scanning calorimeter, using Mettler-Toledo StarE ver. 9.2 software package. The sample (approx. 3 mg) was heated in a pinholed aluminium pan from 30° C. to 300° C. at 10° C./min. The DSC was continuously purged with dry nitrogen, and was routinely calibrated with indium and zinc.

Following this procedure the DSC thermogram shown in FIG. 8 was obtained.

Thermo Gravimetric Analysis

Thermo gravimetric analysis (TGA) experiments were conducted on a Mettler Toledo TGA/SDTA 851e. The sample (approx. 10 mg) was heated in an open Al crucible from 30° C. to 300° C. at 10° C./min. The TGA was continuously purged with dry nitrogen, and was routinely calibrated with Indium and aluminum. Data was evaluated using Mettler-Toledo StarE ver. 9.2 software package.

Following this procedure the TGA thermogram shown in FIG. 10 was obtained.

Fourier Transform Infrared Spectroscopy

Fourier Transform infrared spectroscopy (FTIR) experiments were conducted on a Perkin-Elmer Spectrum One FTIR instrument equipped with an attenuated total reflection (ATR) unit Goldengate supplied from Specac. The system was controlled using Spectrum Ver. 5.0.1 software. The samples (approx.1-2 mg) were placed directly on the diamond surface of the ATR unit and the anvil pressed firmly against the sample. Samples were analysed in the wave number region 4000-600 cm−1. The instrument was routinely calibrated against internal polystyrene filters.

Following this procedure the FT-IR spectrum of crystalline pridopidine hydrochloride Form II shown in FIG. 9 was obtained.

Karl Fischer Titration

Water determinations using Karl Fischer (KF) titrations were performed using Metrohm KF 756 KF Coulometer equipped with a generator electrode without diaphragm. The titrator was equipped with a Metrohm 832 KF Thermoprep oven. The sample was weighed off in small HPLC glass vials, sealed and introduced into the oven (130° C.). Here a needle was used to puncture the rubber septum of the HPLC vial and a dry carrier gas (N2) was used to carry the released water via heated tubing to the titration chamber.

Prior to sample titration, a series of blanks were titrated to determine the blank level. Results were automatically corrected for the blank value. The instrument was routinely controlled by using solid standards with certified water content.

Dynamic Vapour Sorption Measurements

Dynamic vapour sorption (DVS) measurements were conducted using a Q5000 SA from TA instruments.

Experiments were conducted in two sorption/desorption cycles between 0% RH and 95% RH. Prior to the first sorption cycle the sample was equilibrated at 20% RH and the initial weight recorded. Samples were analyzed in an aluminium pan. Humidity was brought down to 0% RH and the sample dried until the weight had stabilized within a given limit. The temperature was held constant at 25° C. Maximum step time was 720 min. Gas flow was 200 cm3/min.

Following this procedure the DVS profiles shown in FIG. 11 were obtained.

CHN Measurements

CHN measurements were performed at Mikroanalytisk Laboratorium, Kemisk Institut, University of Copenhagen, using a Flash EA 1112 analyzer.

Approximately two milligrams of compound was weighed into a small tin beaker and inserted into the combustion chamber. The resulting gasses were collected on a column and analyzed via gas chromatography. Analyses were performed in duplicate.

Image Analysis

Microscopic analysis was carried out using a Zeiss Axiolab microscope (Carl Zeiss, Göttingen, Germany). Photomicrographs were captured using a DeltaPix digital camera and Deltapix software version 1.6 (Maaloev, Denmark). A 5× magnification objective (1.626 μm/pixel) was used without immersion oil and a 40× magnification objective (0.208 μm/pixel) was used with liquid paraffin as immersion oil. The particle size was determined using Motic Image Plus 2.0 software (Motic Group Inc, China), calibrated to pictures of reference scales taken with the used objectives. The particle size distribution and the aspect ratio distribution were calculated using Matlab version 2009b (Mathworks Inc., USA).

Bulk Density and Tapped Density

Density determinations were performed as described in Ph. Eur. 2.9.34. The method was modified as the sample amount placed in the 250 ml volumetric glass cylinder was 50.0 g and 2500 taps were run at 100 taps/min. The measurements were done in triplicate.

The invention claimed is:

1. 4-(3-Methanesulfonyl-phenyl)-1-propyl-piperidine hydrochloride salt in a crystalline form, wherein the crystalline form is anhydrous crystalline Form II characterized by an X-ray powder diffraction pattern with reflections corresponding to the d-spacing values 6.1 and 4.9, and 8.9 and 4.1.

2. A pharmaceutical composition comprising a therapeutically effective amount of the 4-(3-methanesulfonyl-phenyl)-

1-propyl-piperidine hydrochloride salt according to claim 1, together with one or more adjuvants, excipients, carriers and/or diluents.

3. The pharmaceutical composition of claim 2, wherein the therapeutically effective amount of 4-(3-methanesulfonyl-phenyl)-1-propyl-piperidine is from about 1 mg to about 500 mg.

4. The pharmaceutical composition of claim 2, wherein the therapeutically effective amount of 4-(3-methanesulfonyl-phenyl)-1-propyl-piperidine is from about 10 mg to about 100 mg.

5. The pharmaceutical composition of claim 2, wherein the therapeutically effective amount of 4-(3-methanesulfonyl-phenyl)-1-propyl-piperidine is from about 25 mg to about 50 mg.

* * * * *